(12) United States Patent
Eaton et al.

(10) Patent No.: US 9,375,144 B2
(45) Date of Patent: Jun. 28, 2016

(54) MEDICAL DEVICE WITH PATIENT INFORMATION READER

(71) Applicant: Mindray DS USA, Inc., Mahwah, NJ (US)

(72) Inventors: Scott K. Eaton, Briarcliff Manor, NY (US); Kenneth J. Fuchs, Wayland, MA (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 16 days.

(21) Appl. No.: 14/468,015

(22) Filed: Aug. 25, 2014

(65) Prior Publication Data

US 2016/0051146 A1 Feb. 25, 2016

(51) Int. Cl.
*G06F 17/00* (2006.01)
*A61B 5/00* (2006.01)
*A61B 5/0205* (2006.01)
*G06F 19/00* (2011.01)

(52) U.S. Cl.
CPC .............. *A61B 5/0002* (2013.01); *A61B 5/0205* (2013.01); *G06F 19/323* (2013.01); *G06F 19/327* (2013.01); *G06F 19/3406* (2013.01); *G06F 19/322* (2013.01)

(58) Field of Classification Search
CPC . G06F 19/3418; A61B 5/0022; A61B 5/0002
USPC ........................ 235/375; 600/301; 340/539.12
See application file for complete search history.

(56) References Cited

U.S. PATENT DOCUMENTS

2002/0147390 A1* 10/2002 Markis et al. ................. 600/301
2011/0066009 A1* 3/2011 Moon et al. .................. 600/301

* cited by examiner

*Primary Examiner* — Jamara Franklin
(74) *Attorney, Agent, or Firm* — Kory D. Christensen; Stoel Rives LLP (57) ABSTRACT

Medical monitoring devices may be able to read a wireless tag and determine an identity of a patient wearing the tag based on the information read from the tag. The tag may be an RFID tag, a barcode, etc. The tag may itself include identifying information for the patient, or the tag may include an identifier that allows the patient information to be retrieved from a remote storage device via a network. The medical monitoring device may also be able to retrieve configuration information using the identifier. The configuration information may include settings for the medical monitoring devices and/or may include destinations for physiological data measured by the medical monitoring devices. Destinations may organize data based on the patient and may use the patient identifiers transmitted by the medical monitoring devices to associate data from separate medical monitoring devices attached to the same patient.

20 Claims, 9 Drawing Sheets

MEDICAL DEVICE WITH PATIENT INFORMATION READER

TECHNICAL FIELD

The present disclosure relates to medical monitoring devices and more particularly relates to systems and methods that enable such devices to read patient information.

DETAILED DESCRIPTION OF PREFERRED EMBODIMENTS

Modern medical practice makes extensive use of electronic monitoring of vital signs and other physiological parameters of patients. A medical monitoring device may include one or more sensors to acquire physiological data representative of the physiological condition of the patient. Medical monitoring devices may include patient monitors that display measurement data locally, medical telemetry devices that transmit measurement data to remote systems, and/or the like. Medical monitoring devices may need to know which patient is being measured so that physiological data transmitted by the medical monitoring devices can be associated with the correct patient. Medical monitoring devices may also need to be configured differently for different patients, hospital wards, and/or users. Thus, when a medical monitoring device is first connected to a patient, the medical monitoring device may need to identify the patient. Traditionally, each medical monitoring device would have to be configured by manually entering the information for each new patient and/or by programming the medical monitoring device at a central station programming device. The process is time consuming and susceptible to errors, which can result in adverse outcomes for patients. For example, data from a misconfigured monitoring device may be associated with the wrong patient or location, and/or an alarm may not be triggered at the appropriate time.

Medical monitoring devices may be configured to identify a patient to whom the medical monitoring device is connecting. For example, a medical monitoring device may be able to identify the patient and indicate the patient to a data recipient so that the data is properly processed. The medical monitoring device may also or instead load configuration information corresponding to the patient identity. A medical monitoring device may identify the patient by reading an identifier from a tag worn by the patient. In an embodiment, each patient may receive a tag when admitted to a medical center. When the patient is moved to a room or bed with a medical monitoring device, the patient's tag may be read to identify which patient is being coupled to the medial monitoring device.

The medical monitoring device may read the tag as long as it is in close proximity to the tag. The tag may include only the components necessary for the medical monitoring device to read the tag. The tags may be inexpensive to manufacture and to provide to each patient that is admitted to the medical center. The tags may be disposable and/or reusable. Different kinds of medical monitoring devices may be able to read the tags. For example, both patient monitors and telemetry devices may be able to read the tags, so either can quickly identify a patient using the tags. Multiple devices may even read a same tag and become associated with a same patient.

In an embodiment, the medical monitoring device may be connected to an external reader that is able to read tags. For example, the medical monitoring device may communicatively couple to the wireless reader via a wired and/or wireless connection, and the wireless reader may transmit the identifier to the medical monitoring device. An external reader may be expensive and/or inconvenient. A user may need to locate an external reader any time a tag needs to be read, and/or the external reader may be obtrusive if left attached. The external reader may also need to be compatible with the particular medical monitoring device that is being used.

In another embodiment, the medical monitoring device may include a wireless reader built into the medical monitoring device. The integrated wireless reader may be able to read identifiers from one or more types of tags. The tag may be active or passive (e.g., the tag may be powered or may not need a power source other than wireless power received from the reader). The tag may be a radio frequency identification (RFID) tag (e.g., a near field communication (NFC) tag), a barcode (e.g., a one dimensional or two dimensional barcode), text, and/or the like. Thus, the wireless reader may include a radio frequency (RF) reader, a barcode reader (e.g., a laser scanner, a very small camera, etc.), a camera, and/or the like. Other electromagnetic and non-electromagnetic methods of or spectrums for wirelessly communicating information will be apparent to those of skill in the art. The medical monitoring device may be configured with multiple wireless readers for reading different kinds of tags. In some embodiments, a user may be able to select which wireless reader to use each time an identifier is read and/or select a setting indicating which wireless reader to use each time.

The medical monitoring device may be a wireless telemetry device that is small and/or lightweight to allow the patient to easily move around and/or to be easily moved between locations while monitoring of the patient's physiological parameters continues. The telemetry device may not include a display and/or may include only a limited input interface. A built-in wireless reader may allow for faster programming of the telemetry device with fewer errors. The telemetry device may be able to be properly programmed and paired to a patient by reading a patient tag rather than receiving programming at a central programming station, where patient mix-ups are more likely. In addition, when compared to an external reader, a built-in wireless reader may allow the telemetry device to have fewer ports and reduced power consumption. The telemetry device may be able to more efficiently deliver power to a built-in wireless reader than an external reader.

Additionally, external readers do not need to be located and/or left obtrusively attached to the telemetry device.

The tag and/or medical monitoring device may be configured to only work over very short distances. Accordingly, medical practitioners may need to hold the medical monitoring device close to the tag for the tag to be read and inadvertent tag reading may be unlikely. The tags may be located on a part of the patient that will be easy to access, such as a wrist or ankle, so that the patient can be quickly identified by the medical monitoring device. In some embodiments, the medical monitoring device may read the tag in response to a user input. In some embodiments, the user may specify which type of tag should be read, or the type of tag may have previous been set. Alternatively, or in addition, the medical monitoring device may periodically attempt to read any nearby tags (e.g., after a fixed time period has elapsed, each time the medical monitoring device is restarted or a sensor is added or removed, etc.). The medical monitoring device may attempt to read multiple types of tags, and/or the type of tag may have previously been set.

The medical monitoring device may determine identify the patient based on the identifier from the tag (e.g., the medical monitoring device may determine a patient ID number, assigned location, and/or the like). For example, the identifier may include and/or be an indication of the patient's identity, and determining the identity may simply include storing the indication as the patient's identity. Alternatively, or in addition, the medical monitoring device may be able to look up the patient's identity based on the identifier. The medical monitoring device may connect to a network to retrieve the patient identity corresponding to the identifier. For example, a centralized database may maintain records of each patient who is admitted to the medical center and which tag that person was assigned. The medical monitoring device may query the centralized database with an identifier when a tag is encountered. The centralized database may return the identity of the patient assigned that identifier in response to the query.

The medical monitoring device may change one or more settings based on the particular patient being monitored (e.g., patient specific configuration settings). The medical monitoring device may read the one or more settings from the tag and/or may request settings corresponding to the identifier from the central database (e.g., the central database may determine which settings would be best for each patient). The central database may return an indication of the settings and/or an indication of a preset configuration to use. Alternatively, or in addition, the medical monitoring device may receive an indication of a patient diagnosis, condition, and/or demographic (e.g., age, sex, height, weight, race, etc.) and determine locally which settings to use. Accordingly, the settings corresponding to the identifier and/or patient may be stored locally, may be retrieved from a network, and/or may be stored in a hybrid arrangement. In some embodiments, the medical monitor device may send an identifier for itself in addition to the identifier from the tag to the network. The settings from the network may be formatted and/or selected for the particular medical monitoring device requesting them.

The settings may include network settings, such as an internet protocol (IP) address for the medical monitoring device, an IP address for a printer, network connection information, and/or the like. The settings may indicate data recipients. The data recipients may be central stations, viewports, patient records, or other destinations to which the measured physiological data should be sent. The settings may include alarm settings for one or more physiological parameters. The settings may include acuity settings and/or display settings affecting the visual arrangement and display of physiological parameters.

Some settings may be determined by the medical center, such as network settings, data recipients, alarm settings, and/or the like, and other settings may be specified by medical practitioners (e.g., doctors or nurses) responsible for particular diagnoses and/or conditions, such as alarm settings, acuity and display settings, and/or the like. Settings may be selected based on the expected symptoms and/or needs of patients with particular diagnoses and/or conditions. The settings may be default settings that can be changed by a medical practitioner depending on the precise needs of the patient.

A server may determine the location of the various settings and retrieve them for the medical monitoring device in some embodiments. For example, a central station may store settings with which the medical monitoring device should be configured. Various divisions of labor between servers and central stations are envisioned. The central stations may include all configuration information, and the server may simply determine which central station to associate with the medical monitoring device. Alternatively, or in addition, the server may hold some or all of the configuration information for the medical monitoring device. The settings associated with a particular patient may be updated remotely by changing the associated settings saved in a server accessible location and/or in the server. The medical monitoring device may retrieve updated settings periodically, and/or the updated settings may be pushed to devices needing the updates (e.g., the devices may be determined based on which identifiers are associated with updated settings). Alternatively, or in addition, the tags may be updated or replaced to change the settings.

Central stations may also be configured based on the identifier provided to the network by the medical monitoring device. For example, an identifier provided by a medical monitoring device may be transmitted to a central station to which data will be provided. The central station may be add the patient to a list of patients being monitored and/or may already be aware that the patient is coming. The central station may associate the data received from the medical monitoring device with the patient identified to the central station by the medical monitoring device. The central station may display measurement data from the medical monitoring device next to the patient's name or other identifying information, and/or data and/or statistical information may be saved to the patient's medical record.

The medical monitoring devices may also be configured to determine their location. For example, the medical monitoring devices may read a tag that indicates location (e.g., each room and/or bed in the medical center may include a tag), may determine its position by communicating with a satellite positioning system, may determine its position using an indoor positioning system, and/or the like. The medical monitoring device may report its location to a medical center network in addition to the patient identity. The patient could then be associated with the identified location, e.g., by the server, the central station, etc. For example, the central station may display the name of each patient and their location and may receive the name and location from the medical monitoring device and/or the central database. The settings of the medical monitoring device may be updated based on the patient, based on the location, and/or a combination of the two.

Figure 1:
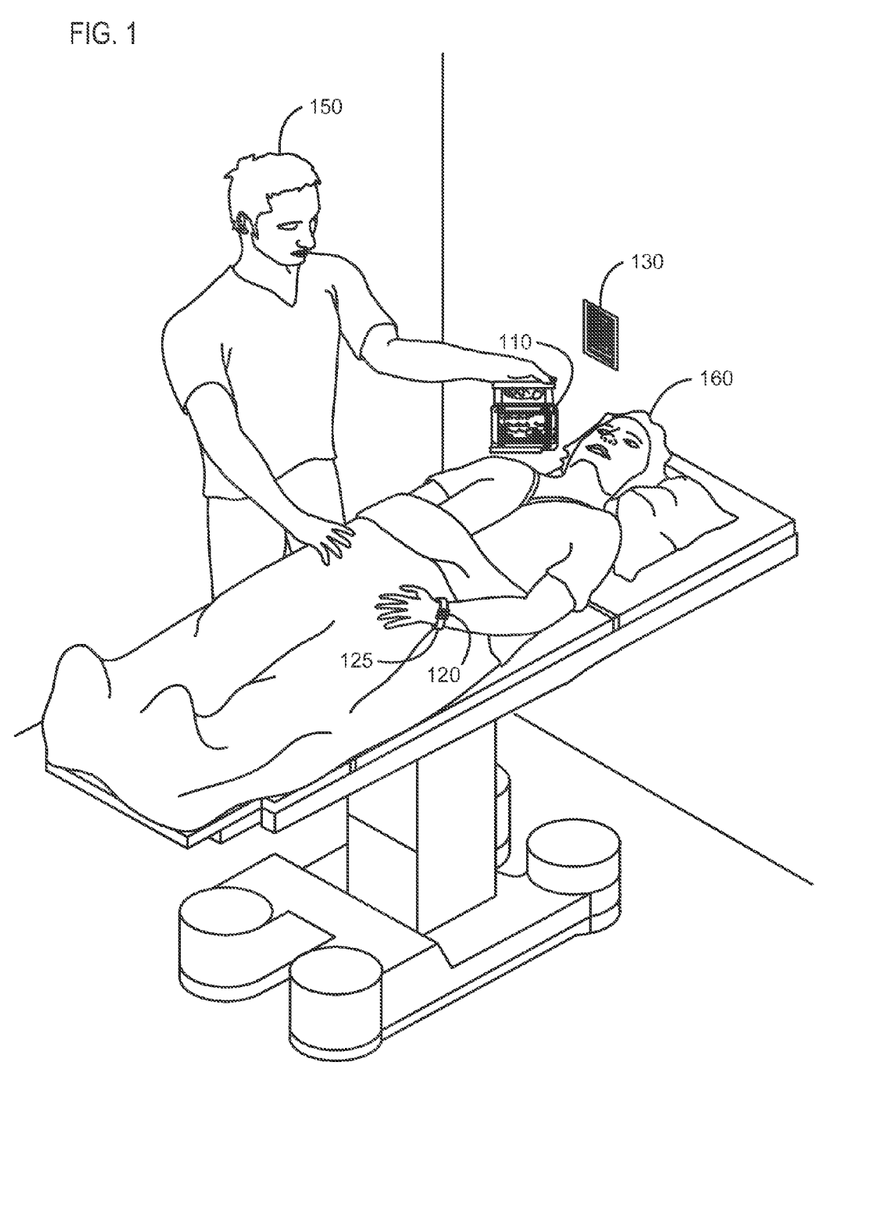
FIG. 1 is a perspective view of a medical practitioner configuring a patient monitor for a patient.

FIG. 1 is a perspective view of a medical practitioner 150 configuring a patient monitor 110 for a patient 160. The patient monitor 110 may be configured to connect to a patient 160 and to measure one or more physiological parameters of the patient. The patient 160 may have been recently admitted to the illustrated medical center and thus may have just entered her room and/or bed and not yet been connected to the patient monitor 110. When the patient 160 checked-in, her information (e.g., name, demographic information, medical history, symptoms, etc.) may have been entered into a computer, and she may have received a wearable tag 120 that can be read by the patient monitor 110. In the illustrated embodiment, the tag 120 is included as part of a bracelet 125 that can be worn by the patient 160. The bedside may also include a tag 130 that can be read by the patient monitor 110. Because the patient 160 may have just arrived at the room and/or bed, the patient monitor 110 may include settings for another patient and/or default settings not associated with any patient. The patient monitor 110 may not know which central station should receive physiological parameter data associated with the patient 160.

The illustrated wireless tags 120, 130 may be unpowered, RF tags. The tags 120, 130 may store an identifier that is unique to the particular tag 120, 130. The patient monitor 110 may receive an indication from the medical practitioner 150 that it should read one of the tags 120, 130. The patient monitor 110 may transmit RF energy to the tag 120, 130 to energize the tag 120, 130. The tag 120, 130 may use the received energy to read its identifier and transmit the identifier back to the patient monitor 110. The patient monitor 110 may use the identifier to determine patient identity, patient demographics, patient diagnosis or condition, location, a central station associated with the room and/or bed, configuration settings, and/or the like (e.g., by accessing a local or remote database). In some embodiments, one or both of the tags 120, 130 may include an address for the central station and/or configuration settings for the patient monitor 110 in addition to, or instead of, the identifier. The medical practitioner 150 may be able to entirely configure the patient monitor simply by reading the wireless tags 120, 130. The medical practitioner 150 can then make any special changes to the settings that he deems necessary.

Figure 2:
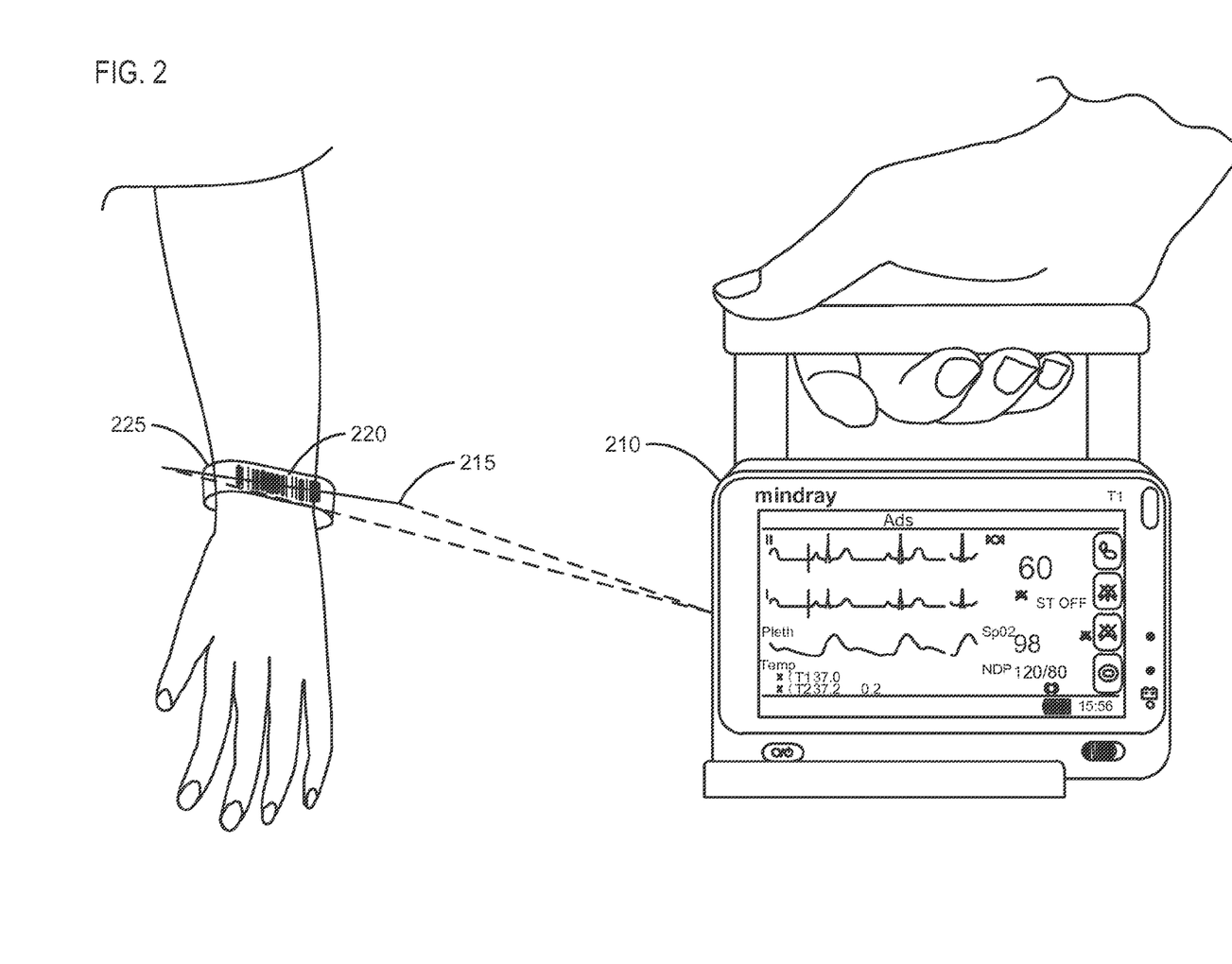
FIG. 2 is a perspective view of a patient monitor configured to read a tag that includes bar code.

FIG. 2 is a perspective view of a patient monitor 210 configured to read a wearable tag 220. In this embodiment, the tag 220 may include a barcode. For example, the tag 220 may include paper, plastic, and/or an adhesive onto which the barcode has been printed. In the illustrated embodiment, the barcode may be included on a bracelet 225. The barcode may be printed directly onto the bracelet 225, may be imprinted in the bracelet, and/or may be mechanically coupled to the bracelet 225 (e.g., adhered to a surface of the bracelet 225, inserted into a transparent pocket, etc.). The tag 220 may be inexpensive to produce and unobtrusive when worn by the patient. The tags 220 and/or bracelets 225 may be reusable and/or may be disposed of by the patient when leaving the medical center. In the illustrated embodiment, the patient monitor 210 projects a laser 215 onto the tag 220 to read the barcode (e.g., by reading the reflections with a photodiode). In other embodiments, the patient monitor 210 may use a small camera to read the tag 220 and may use image processing techniques to decipher the barcode. The patient monitor 210 may only be configured to read barcodes or may be configured to read multiple types of tags (e.g., RFID tags and barcodes). Various combinations of wireless readers may be included in the patient monitor 210.

Figure 3:
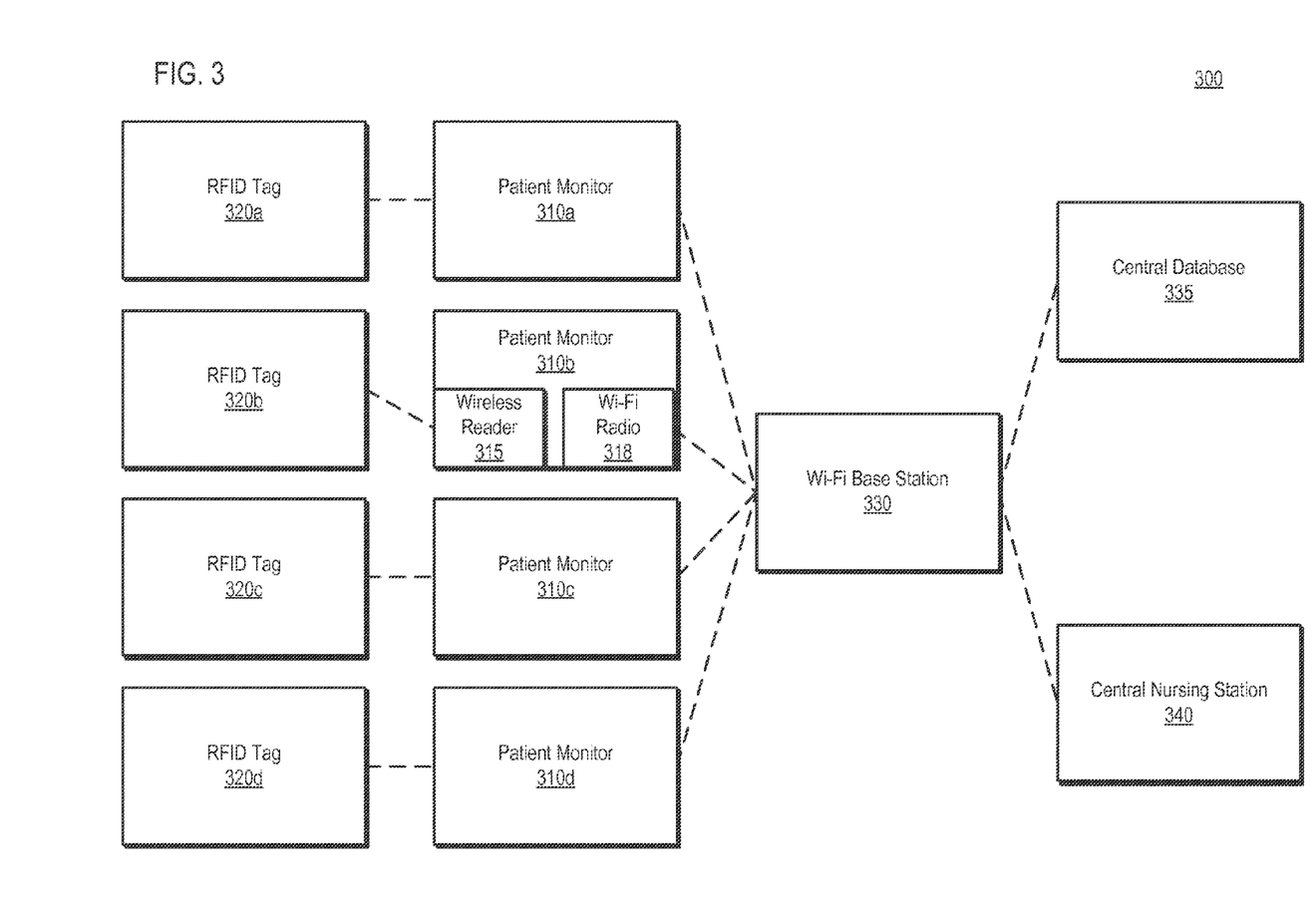
FIG. 3 is a block diagram of a system for configuring a plurality of patient monitors based on patient identity.

FIG. 3 is a block diagram of a system 300 for configuring a plurality of patient monitors 310a-d based on patient identity. A plurality of RFID tags 320a-d may each have been previously associated with a patient. A wireless reader 315, such as the one illustrated in the patient monitor 310b, may be able to read the RFID tags 320a-d. The RFID tags 320a-d may store an identifier that is retrieved by the wireless reader 315 during reading. The identifier may be unique to each RFID tag 320a-d but may otherwise not include any information content. Alternatively, or in addition, the RFID tags 320a-d may include information content, such as a patient name, patient demographics, patient diagnosis and/or condition, settings for the patient monitor 310, an address from settings can be retrieved, and/or the like. The wireless reader 315 may transmit RF power to an RFID tag 320b being read. The RFID tag 320b may use the wireless power to read the identifier from local storage and to transmit the identifier to the wireless reader 315. The wireless reader 315 may receive the identifier from the RFID tag 320b and provide it to the patient monitor 310b.

A Wi-Fi radio 318, such as the one illustrated in the patient monitor 310b, may able to wirelessly communicatively couple with a Wi-Fi base station 330. Wired or wireless communication methods other than Wi-Fi may be used in alternate embodiments. In the illustrated embodiment, the patient monitor 310b may not include local storage that associates an identifier that was read with information of interest to the patient monitor 310b (e.g., patient information, settings, addresses, etc.). Instead, the patient monitor 310b may send the identifier to a central database 335, which may store the information of interest and associate it with identifiers from RFID tags 320a-d. The central database 335 may look up the identifier and return any associated information to the patient monitor 310b. The patient monitor 310b may adjust its settings and/or configuration based on the information received from the central database 335. To change the information associated with a particular identifier, the central database 335 can be updated, and any future requests from patient monitors will receive the updated information. Alternatively, or in addition, the update may be pushed to the appropriate patient monitor 310b by the central database.

The settings stored by the central database 335 may include destinations for data from the patient monitors 310a-d. For example, the settings received by the patient monitor 310b may indicate that the patient data should be sent to a central nursing station 340. The patient monitor 310b may use the Wi-Fi radio 318 and Wi-Fi base station 330 to transmit physiological data from the patient to the central nursing station 340. The patient monitor 310b may also indicate the patient identity and/or location to the central nursing station 340 based on the information received from the central database 335. The central nursing station 340 may add the indicated patient to a list of patients being tracked by the central nursing station and may associate the patient monitor 310b with the patient so incoming data from the patient monitor 310b is handled correctly. Multiple of the patient monitors 310a-d may be associated with the same patient, so the central nursing station 340 may need to know patient identities to process, store, and/or display related data from separate patient monitors 310a-d together. For example, one of the patient monitors 310a-d may be a telemetry device rather than a patient monitor. In some embodiments, the central nursing station 340 may provide information associated with the identifier to the patient monitor 310 instead of, or in addition to, it being sent by the central database 335. The central nursing station 340 may specify settings, data destinations, a proper encoding for data, and/or the like.

Figure 4:
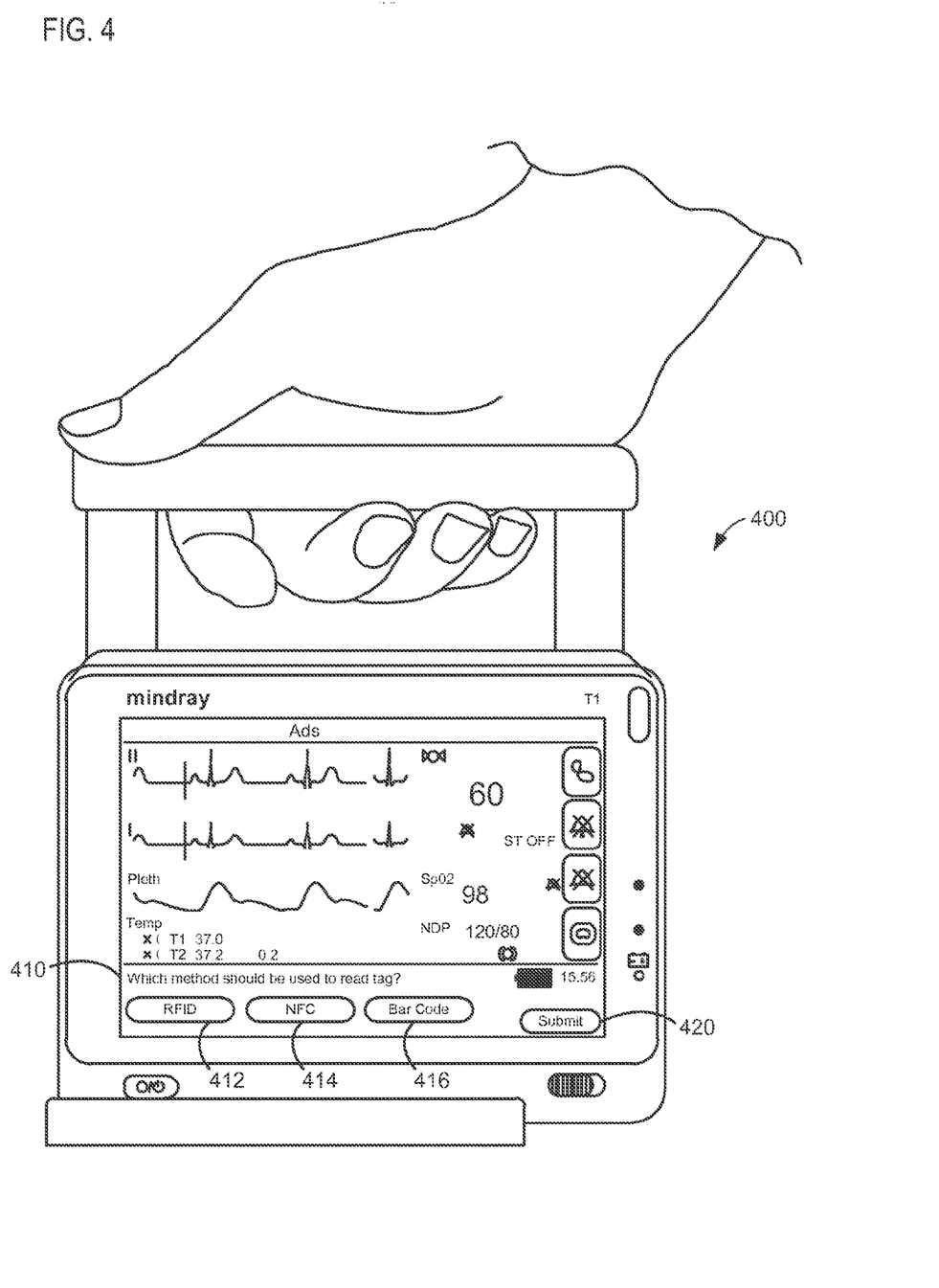
FIG. 4 is a perspective view of a patient monitor presenting an exemplary screen display that may be provided to the user for selecting a wireless reader to read a tag.

FIG. 4 is a perspective view of a patient monitor 400 presenting an exemplary screen display that may be provided to a user for selecting a wireless reader to read a tag. The patient monitor 400 may include a touch screen display that is able to display information to the user as well as receive inputs from the user. In other embodiments, other user interface outputs and inputs may be used to interact with the user. In the illustrated embodiment, the patient monitor 400 may include a plurality of wireless readers able to read different kinds of tags. Rather than attempt to read a tag using all possible wireless readers, the patient monitor 400 may display a prompt 410 asking the user which method to use to read the tag. The prompt 410 may be displayed in response to a user indication that the patient monitor 400 should attempt to read a tag.

The prompt 410 may allow the user to choose between using an RFID option 412, an NFC option 414, and a barcode option 416. The user may select a desired option 412, 414, 416 and press a submit button 420 to indicate that the option has been selected. The patient monitor 400 may select the appropriate wireless reader and/or appropriate wireless reader configuration for reading the tag based on the user input. Alternatively, or in addition, the patient monitor 400 may include settings (e.g., user adjustable settings) specifying which wireless reader to use, and/or the patient monitor 400 may remember a previous user selection. The patient monitor 400 may default to the wireless reader specified in the settings until the settings are changed. If the patient monitor 400 includes only a single kind of wireless reader, the patient monitor 400 may not need to prompt the user.

Figure 5:
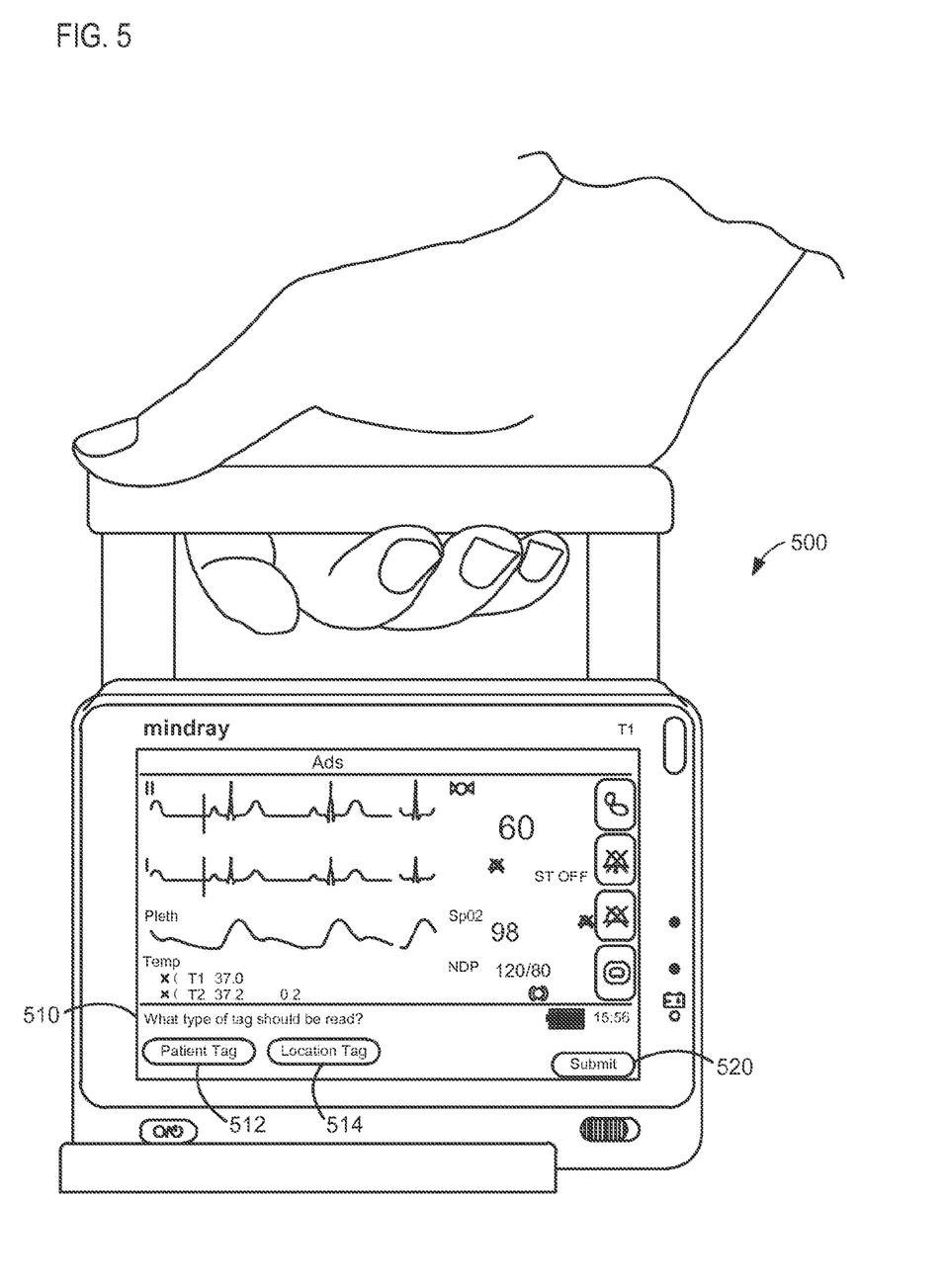
FIG. 5 is a perspective view of a patient monitor presenting an exemplary screen display that may be provided to a user for selecting which type of tag should be read.

FIG. 5 is a perspective view of a patient monitor 500 presenting an exemplary screen display that may be provided to a user for selecting which type of tag should be read. The patient monitor 500 may present a prompt 510 asking which type of tag should be read. The patient monitor 500 may be configured to read tags that serve different purposes. For example, some tags may store location information while others may store information about patients. Alternatively, or in addition, the tags may include identifiers that correspond to different types of information. In some embodiments, location identifiers may be distinguishable from patient identifiers, and/or every identifier may be unique so that no conflicts occur. In such embodiments, the patient monitor 500 may not need to prompt the user about the type of tag, and the patient monitor 500 and/or a central database may determine the type of tag based on the identifier.

In the illustrated embodiment, the patient monitor 500 offers a selection for patient tag 512 and a selection for location tag 514. A user may select the patient tag 512 option to read a tag worn by a patient that identifies the patient. The user may select the location tag 514 option to read a tag that indicates the location of the patient monitor 500. Once the user has selected the information to be retrieved, the user may press a submit button 520 to indicate that the desired selection has been made. Based on the selection, the patient monitor 500 may indicate to a central database which kind of identifier it is sending. Alternatively, or in addition, the patient monitor 500 may determine how to process data from the tag and/or central database based on the selection.

Figure 6:
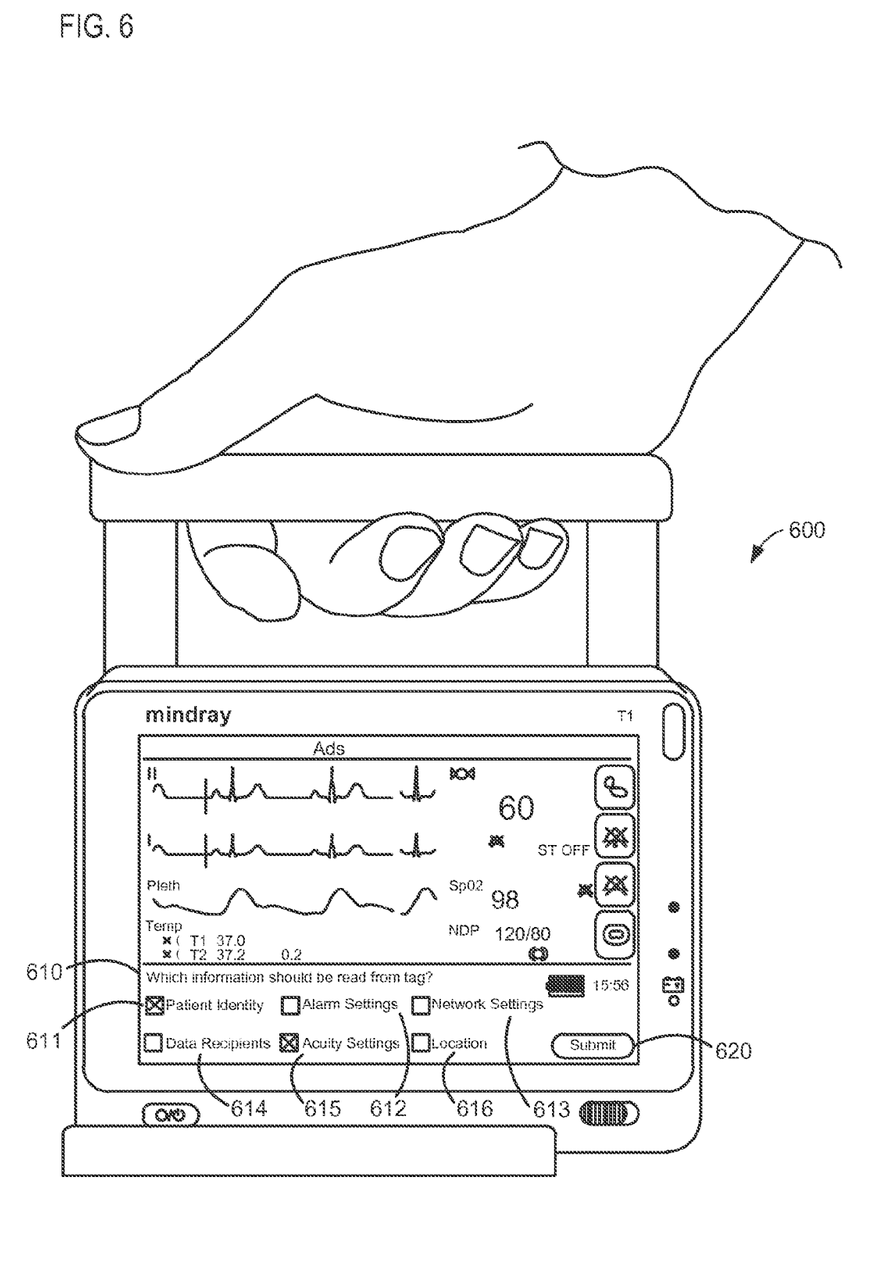
FIG. 6 is a perspective view of a patient monitor presenting an exemplary screen display that may be provided to a user for selecting which information should be retrieved.

FIG. 6 is a perspective view of a patient monitor 600 presenting an exemplary screen display that may be provided to a user for selecting which information should be retrieved. The patient monitor 600 may present a prompt 610 asking which information should be read from the tag. The patient monitor 600 may prompt the user about information that is on the tag itself or may prompt the user about information that will be requested from a network once the tag is read. The tag reading process may be transparent to the user, so the user may not be aware of whether the information is coming from the tag or is coming from remote devices that the patient monitor can access via the network.

In the illustrated embodiment, the user may select between reading a patient identity 611, alarm settings 612, network settings 613, data recipients 614, acuity settings 615, and/or location 616. The patient identity 611 may include a patient name, patient demographics, a diagnosis or condition, and/or the like. The alarm settings 612 include upper and/or lower boundaries for one or more physiological parameters outside of which an alarm should be sounded and/or more complicated criteria for sounding alarms. The alarm settings 612 may also indicate how the alarm should be signaled (e.g., locally, at a nursing station, etc.). The network settings 613 may include IP addresses and/or identification information for, e.g., printers, wireless routers, central databases, etc. The data recipients 614 may be destinations to which physiological data from the patient should be sent. The data recipients 614 may include central stations, viewports, patient records, and/or the like. The frequency with which data should be transmitted may also be provided to the patient monitor 600. The acuity settings 615 may include adjustments to the layout of the display, the size of displayed data, the number of data parameters displayed, etc. The location 616 may be the location of the tag and may include a room number, an indication of a bed, a ward, a digital address (e.g., an IP address) the patient monitor 600 should use, and/or the like. The user may be able to select more than one type of information to read at once.

Once the user has selected the information to be retrieved, the user may press a submit button 620 to indicate that the desired selection has been made. The patient monitor 600 may read the settings from the tag and/or network. The patient monitor 600 may update its settings and/or configuration based on the received information. The loaded information may be loaded as default settings, and the user may be able to change the settings to fit the individual needs of the patient. Thus, the user may choose to load a particular set of information if only a few or no changes will be made to the information or may not load the information if the user prefers to enter it entirely by hand.

Figure 7:
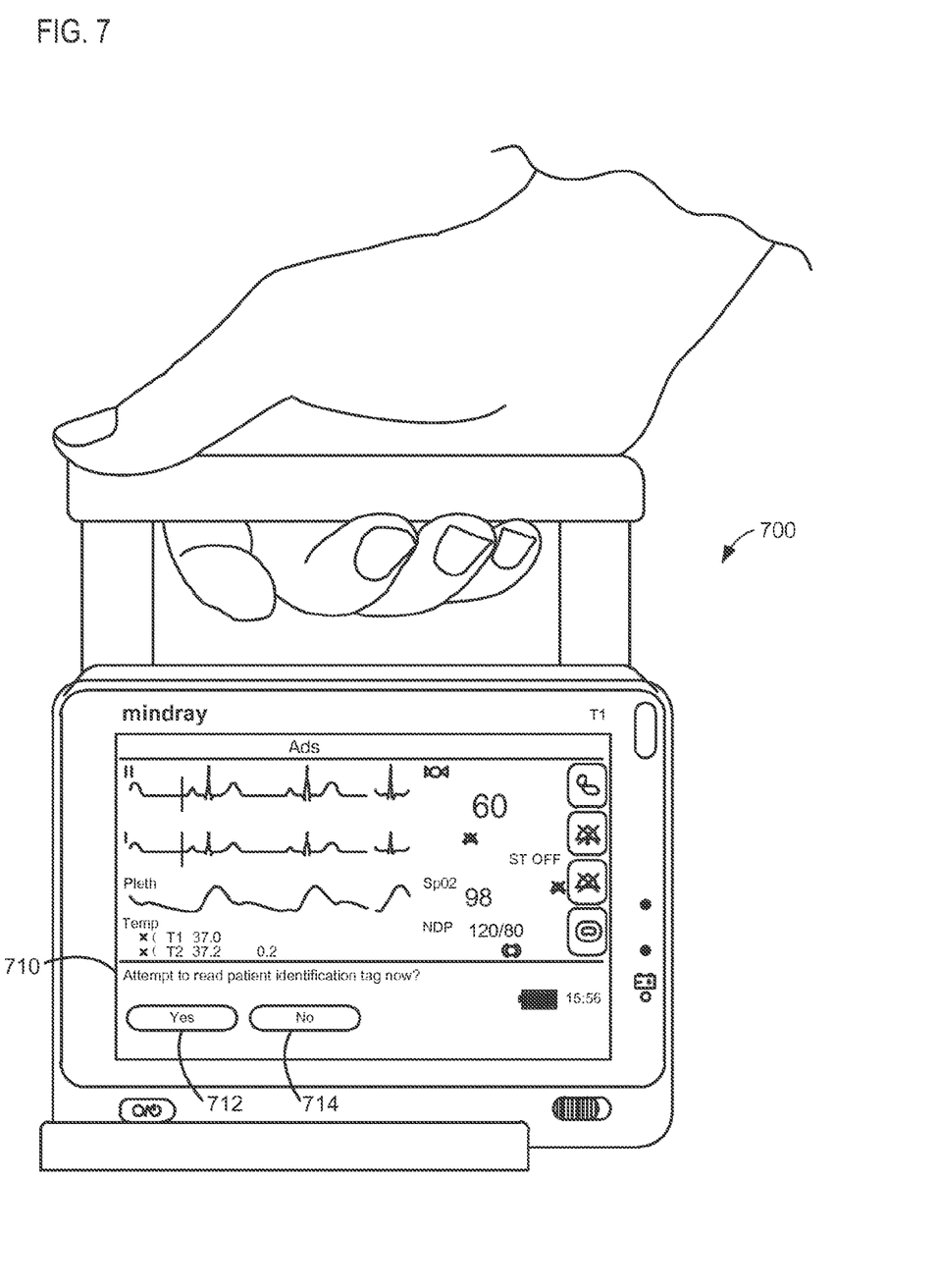
FIG. 7 is a perspective view of a patient monitor presenting an exemplary screen display confirming that a tag should be read.

FIG. 7 is a perspective view of a patient monitor 700 presenting an exemplary screen display confirming that a tag should be read. To conserve energy, the patient monitor 700 may confirm that the user is ready and that the tag is nearby before attempting to read the tag. For example, the patient monitor 700 may display a prompt 710 asking whether it should read the identification tag now. The patient monitor 700 may provide a yes option 712 and a no option 714. The patient monitor 700 may immediately attempt to read the tag in response to an input selecting the yes option 712 and may abort reading the tag in response to the no option 714.

In other embodiments or configurations, the patient monitor 700 may not prompt the user. For example, the patient monitor 700 may periodically attempt to read any nearby tags and/or may attempt to read nearby tags after predetermined events (e.g., powering on, waking from a rest state, etc.). The patient monitor 700 may determine whether the identifier is new and/or whether centrally stored information associated with the identifier has been updated. The patient monitor 700 may prompt the user after the tag is read to determine whether the user wants to use the newly discovered settings. In some embodiments, the patient monitor 700 may switch between receiving user requests to read tags and periodically reading tags (e.g., the settings may specify which mode, the patient monitor 700 may select a mode based on whether external power is connected, the patient monitor 700 may periodically attempt to read tags but allow user requests between attempts, etc.).

Figure 8:
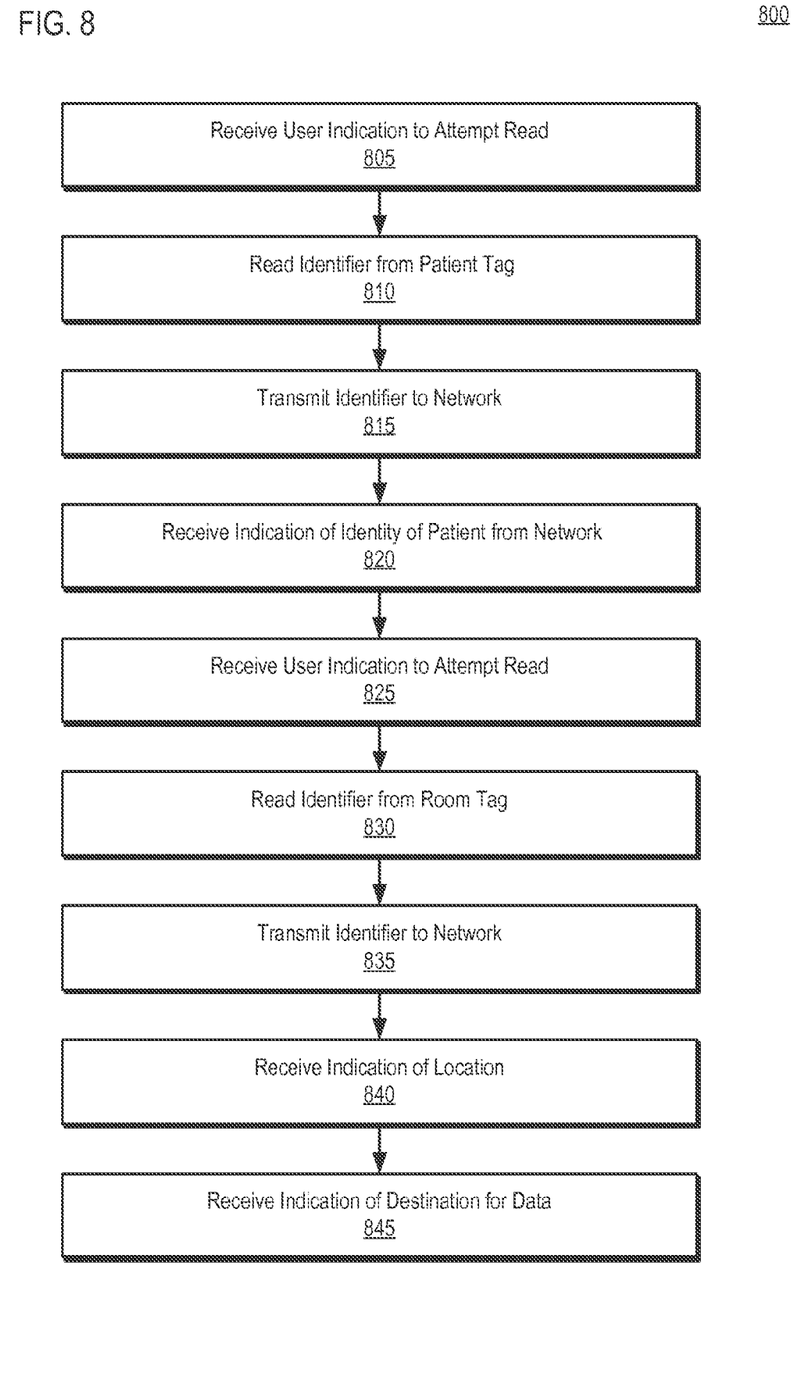
FIG. 8 is a flow diagram of a method for determining an identity and/or a location of a patient.

FIG. 8 is a flow diagram of a method 800 for determining an identity and/or a location of a patient. The method 800 may begin by receiving 805 a user indication to attempt to read a tag. Receiving 805 the user indication may include receiving indications of which wireless reader to use, which type of tag should be read (e.g., a patient tag), what types of information should be read, confirmation that a read should be attempted, and/or the like. Receiving 805 the user indication may include a user indicating that reads should be attempted periodically and/or in response to predetermined events.

An identifier may be read 810 from a patient tag. A medical practitioner may hold a medical monitoring device in close proximity to a tag worn by a patient during reading. Reading 810 the tag may include delivering energy to the tag, such as RF energy to an RFID tag or laser light to a barcode. The tag may use the energy to determine an identifier (e.g., an RFID tag may read the identifier from local storage, a barcode may absorb or reflect the energy based on the identifier, etc.). The tag may then transmit the identifier back. Reading 810 the identifier may be receiving the identifier transmitted from the tag. The identifier may be encoded (e.g., with error correction), so reading 810 the tag may include decoding the identifier in some embodiments.

The identifier may be transmitted 815 to a network. For example, the identifier may be transmitted 815 over a wireless communicative coupling to a medical center intranet. Depending on the embodiment, the identifier may be transmitted 815 to a server, a central database, a central nursing station, a viewport, and/or the like. The network may automatically determine the destination for identifiers, and/or medical monitoring devices may be configured to know the destination. Alternatively, or in addition, the identifier may include the desired location, and/or the desired destination may be read from the tag in addition to the identifier.

The ultimate destination for the identifier may include a storage device that stores identities of patients in association with identifiers. The identifier may be used to look up the identity of the patient, which may be returned via the network. Transmitting 815 the identifier may include indicating which type of information (e.g., a patient identity) should be returned. An indication of the patient identity may be received 820 from the network. The indication may include a patient ID number, an assigned location, and/or the like. A medical monitoring device may be configured based on the identity of the patient.

A medical practitioner may also want to read a location so that the patient can be associated with the location as well. Accordingly, a user indication to attempt to read a tag may be received 825 from the user again. As before, receiving 825 the user indication may include receiving indications of which wireless reader to use, which type of tag should be read (e.g., a location tag), what types of information should be read, confirmation that a read should be attempted, and/or the like. The medical practitioner may hold the medical monitoring device in close proximity to a tag for the particular location, and an identifier may be read 830 from the location tag.

The identifier from the location tag may also be transmitted 835 to a network. The ultimate destination for the identifier may include a storage device that stores information (e.g., location information) in association with identifiers. The identifier may be used to look up the location, which may be returned via the network. An indication of the location may be received 840 from the network. The central database, a server, a central nursing station, and/or the like may associate the location with the patient in response to the transmitting 815, 835 of the patient and location identifiers to the network.

An indication of one or more destinations for physiological data may be received 845 from the network. The medical monitoring device may begin transmitting to the indicated destinations after receiving the indications of the destinations. The destinations may include a central nursing station, a patient record, and/or the like. The patient monitor may use identifying information (e.g., for the patient and/or location) when communicating with data recipients to indicate a source for the data and/or a patient or location with whom the data should be associated. The recipient may be responsible for ensuring the physiological data is handled properly. Alternatively, or in addition, the medical monitoring device may receive a destination address specific to the patient and be responsible for delivering the physiological data to the proper destination.

The patient and/or location identifier may be used to look up the associated configured information, which may be returned via the network. Transmitting 815, 835 the identifiers may include indicating which information should be returned. The configuration information may be received from the network and may be used to modify the operation of medical monitoring devices. For example, the information may include settings (e.g., alarm settings, network settings, acuity settings, etc.), data recipients, and/or the like.

A medical monitoring device, such as a patient monitor, may be configured based on the received configuration information. For example, patient monitor settings may be modified based on the configuration information. In an embodiment, the configuration information may include values for various settings, and the patient monitor may replace its own settings values with the ones received. The configuration information may also include destinations for physiological data measured by the patient monitor. The patient monitor may begin using the updated configuration settings after receiving the configuration information. Alternatively, or in addition, the patient monitor may alert the user to the changes being made and/or confirm with the user that the changes may be made. The configuration information may include default settings and destinations that can be updated by a user.

Figure 9:
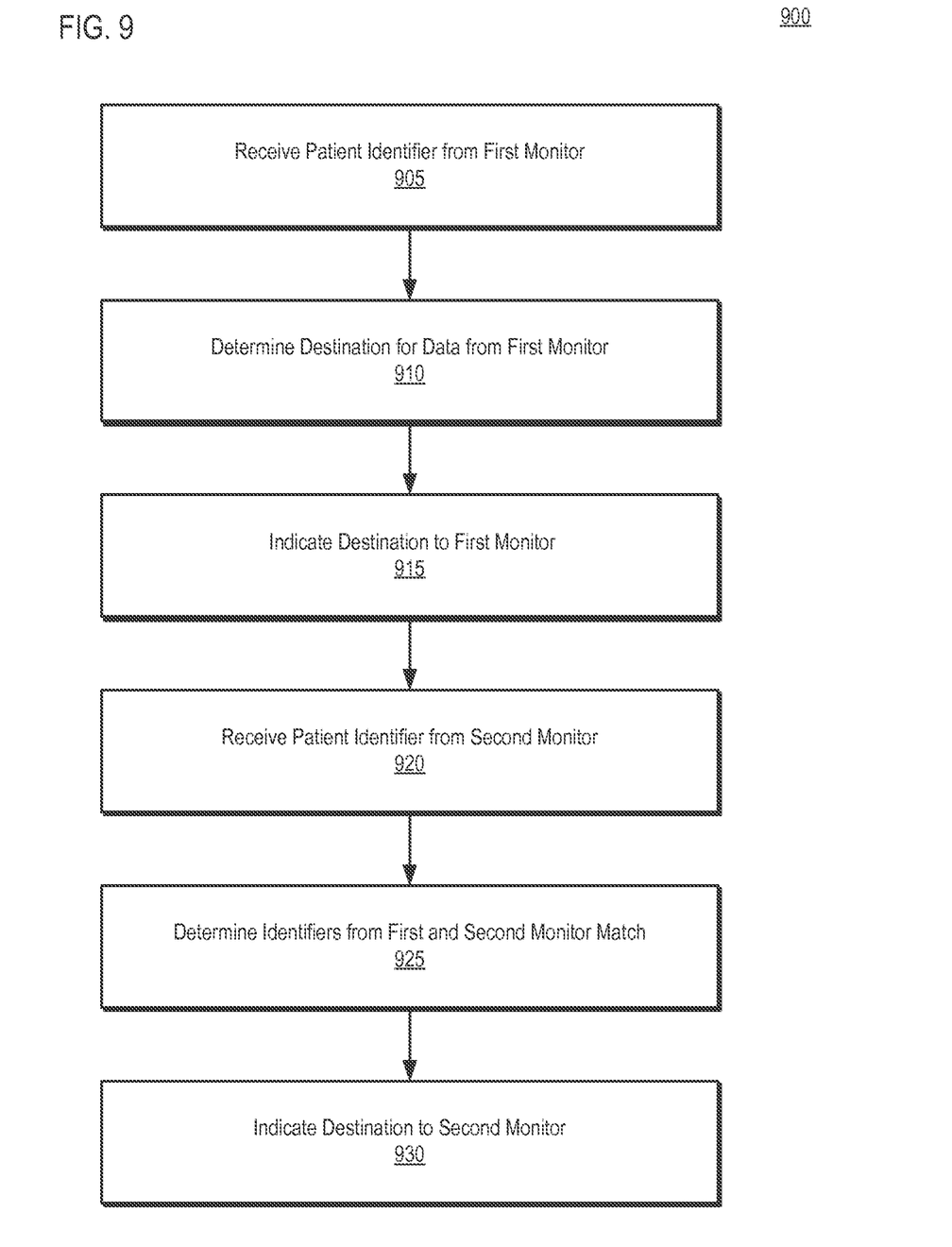
FIG. 9 is a flow diagram of a method for collating data associated with a single patient received from multiple medical devices

FIG. 9 is a flow diagram of a method 900 for collating data associated with a single patient received from multiple medical devices. For example, a patient may be connected to a patient monitor and a telemetry device, to multiple telemetry devices, and/or the like. The method may begin by receiving 905 a patient identifier from a first medical monitoring device. The medical monitoring device may have read the identifier from a patient as previously discussed. Receiving 905 the patient identifier may include receiving an indication the patient is now associated with the medical monitoring device.

A destination for data from the first medical monitoring device may be determined 910. The destination may be a patient record, a central nursing station, a viewport, and/or the like. A destination patient record may be determined by comparing identifying information for the patient received from the first medical monitoring device with identifying information for the patient stored in the patient record. A destination central nursing station may be determined based on proximity to the first medical monitoring device and/or a ward in which the patient is located. The central nursing station may also receive the patient identifier so that it can associate future data from the first medical monitoring device with that patient identifier. The destination may be indicated 915 to the first medical monitoring device, and the first medical monitoring device may begin transmitting physiological data to the destination.

A patient identifier may later be received 920 from a second medical monitoring device. It may be determined 925 that the patient identifiers from the first and second medical monitoring devices match (e.g., both medical monitoring devices read the same patient tag). Because the patient identifiers match, similar and/or identical destinations may be used to ensure that the data from the two medical monitoring devices is stored, processed, and/or displayed together. The patient record, central nursing station, viewport, and/or the like that is receiving data from the first medical monitoring device may be informed that it will begin receiving data for the same patient from a second medical monitoring device. The destination for the data may then ensure that the sets of data are handled properly in relation to one another. The destination may be indicated 930 to the second medical monitoring device, and the second medical monitoring device may begin transmitting data to the indicated destination. The first and second medical monitoring devices may include information identifying a source of the data so that destination can distinguish which medical monitoring device sent the data.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD ROMs, DVD ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. Each network includes at least two computers or computer systems, such as the server and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" or wireless protocols known to those of skill in the art. The network may encompass smaller networks and/or be connectable to other networks through a gateway or similar mechanism.

Each computer system includes at least a processor and a memory; computer systems may also include various input devices and/or output devices. The processor may include a general purpose device, such as an Intel®, AMD®, or other "off-the-shelf" microprocessor. The processor may include a special purpose processing device, such as an ASIC, SoC, SiP, FPGA, PAL, PLA, FPLA, PLD, or other customized or programmable device. The memory may include static RAM, dynamic RAM, flash memory, one or more flip-flops, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computer systems may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, include one or more physical or logical blocks of computer instructions, which may be organized as a routine, program, object, component, data structure, etc., that perform one or more tasks or implement particular abstract data types.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication; access control; and other security tools and techniques provided by public keys, encryption, firewalls, and/or other means.

It will be understood by those having skill in the art that many changes may be made to the details of the above-described embodiments without departing from the underlying principles of the invention. The scope of the present disclosure should, therefore, be determined only by the following claims.

The invention claimed is:

1. A medical telemetry device comprising:
a measurement component configured to receive, from at least one sensor, physiological data representative of a physiological condition of a patient;
a built-in wireless reader configured to retrieve an identifier from a tag worn by the patient;
a processing unit configured to identify the patient based on the identifier and to alter settings of the telemetry device depending on the patient; and
a communication interface configured to transmit the physiological data and indication of the patient's identity.

2. The medical telemetry device of claim 1, wherein the communication interface is configured to receive an indication of the identity of the patient from a network in response to providing the identifier.

3. The medical telemetry device of claim 1, wherein the communication interface is configured to retrieve configuration information corresponding to the identifier from a network.

4. The medical telemetry device of claim 3, wherein the configuration information includes an indication of a destination to which the physiological data should be provided.

5. The medical telemetry device of claim 1, wherein the wireless reader is configured to read a tag at a patient bedside, and wherein the processing unit is configured to determine the location of the patient's bed based on the tag.

6. The medical telemetry device of claim 1, wherein the tag is selected from the group consisting of a radio frequency identification tag and a barcode.

7. The medical telemetry device of claim 1, further comprising a body, wherein the wireless reader is integral with the body.

8. The medical telemetry device of claim 1, wherein the identifier comprises an indication of the identity of the patient.

9. The medical telemetry device of claim 1, wherein the processing unit is configured to identify the patient by determining an identifier associated with the patient.

10. The system of claim 1, in which the settings corresponding to diagnostic or demographic data of the patient.

11. The system of claim 1, in which the communication interface is configured to transmit the physiological data wirelessly over a network and the settings include network settings.

12. A method for determining an identity of a patient using a medical telemetry device, the method comprising:
the medical telemetry receiving physiological data representative of a physiological condition of a patient from at least a sensor;
the medical telemetry device receiving a user indication to read a tag on the patient;
the medical telemetry device reading an identifier from the tag through a built-in wireless reader;
the medical telemetry device determining the identity of the patient based on the identifier and altering settings of the telemetry device depending on the patient; and
the medical telemetry device transmitting the physiological data and an indication of the patient's identity.

13. The method of claim 12, wherein determining the identity comprises receiving an indication of the identity of the patient from a network in response to providing the identifier.

14. The method of claim 12, further comprising retrieving configuration information corresponding to the identifier from a network.

15. The method of claim 14, wherein the configuration information includes an indication of a destination to which data from the medical telemetry device should be provided.

16. The method of claim 12, further comprising reading a tag at a patient bedside to determine a location of the patient's bed.

17. The method of claim 12, wherein the tag is selected from the group consisting of a radio frequency identification tag and a barcode.

18. The method of claim 12, wherein the identifier comprises an indication of the identity of the patient.

19. The system of claim 12, in which the settings corresponding to diagnostic or demographic data of the patient.

20. The system of claim 12, in which transmitting the physiological data is done wirelessly over a network and the settings include network settings.

* * * * *